(12) United States Patent
Oda et al.

(10) Patent No.: US 8,304,746 B2
(45) Date of Patent: Nov. 6, 2012

(54) FLUORESCENT MEASUREMENT DEVICE FOR LIVING BODY AND EXCITING LIGHT-IRRADIATING DEVICE FOR FLUORESCENT MEASUREMENT

(75) Inventors: Ichiro Oda, Kyoto (JP); Shinji Nagamachi, Kyoto (JP); Kentaro Hizume, Kyoto (JP); Yoshio Tsunazawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 391 days.

(21) Appl. No.: 12/531,903

(22) PCT Filed: Mar. 19, 2007

(86) PCT No.: PCT/JP2007/055470
§ 371 (c)(1),
(2), (4) Date: May 18, 2010

(87) PCT Pub. No.: WO2008/114372
PCT Pub. Date: Sep. 25, 2008

(65) Prior Publication Data
US 2010/0294947 A1 Nov. 25, 2010

(51) Int. Cl.
*G01J 1/58* (2006.01)
(52) U.S. Cl. .................................. 250/458.1
(58) Field of Classification Search ............ 250/458.1
See application file for complete search history.

(56) References Cited

U.S. PATENT DOCUMENTS

| 6,894,289 B2 | 5/2005 | Nilson et al. |
| 7,348,587 B2 * | 3/2008 | Shimizu et al. .............. 250/584 |
| 2004/0081621 A1 | 4/2004 | Arndt et al. |

FOREIGN PATENT DOCUMENTS

| JP | 11-326210 A | 11/1999 |
| JP | 2001-154103 A | 6/2001 |
| JP | 2003-232736 A | 8/2003 |
| JP | 2004-532969 A | 10/2004 |
| JP | 2004-325174 A | 11/2004 |
| JP | 2005-172614 A | 6/2005 |
| WO | WO-02/31182 A2 | 4/2002 |

OTHER PUBLICATIONS

International Search Report for the Application No. PCT/JP2007/055470 mailed Jun. 5, 2007.
Chen, Yanping et al., "Whole-body Fluorescent Optical Imaging Based on Power Light Emitting Diode", Engineering in Medicine and Biology 27th Annual Conference, 2005, pp. 1442-1445.

* cited by examiner

*Primary Examiner* — David Porta
*Assistant Examiner* — Hugh H Maupin
(74) *Attorney, Agent, or Firm* — Cheng Law Group, PLLC

(57) ABSTRACT

Disclosed herein is a fluorescence measurement device for a living body configured to be able to reduce wavelength components that will become leak light and to easily switch a wavelength and an irradiation direction. The fluorescence measurement device for a living body comprises: a sample holder on which a living body sample is to be placed; an exciting light-irradiating device having a plurality of exciting light sources arranged at mutually different positions, each of which is composed of a laser diode or a light-emitting diode and is provided with a filter having an optical property to eliminate, from a spectrum of the exciting light source, disturbing wavelength components overlapping with wavelength components of fluorescence to be detected; an electrical switch for switching lighting of the exciting light sources; a detector for picking up an image produced by fluorescence emitted from the sample placed on the sample holder; and an image display device for displaying the image picked up by the detector.

3 Claims, 10 Drawing Sheets

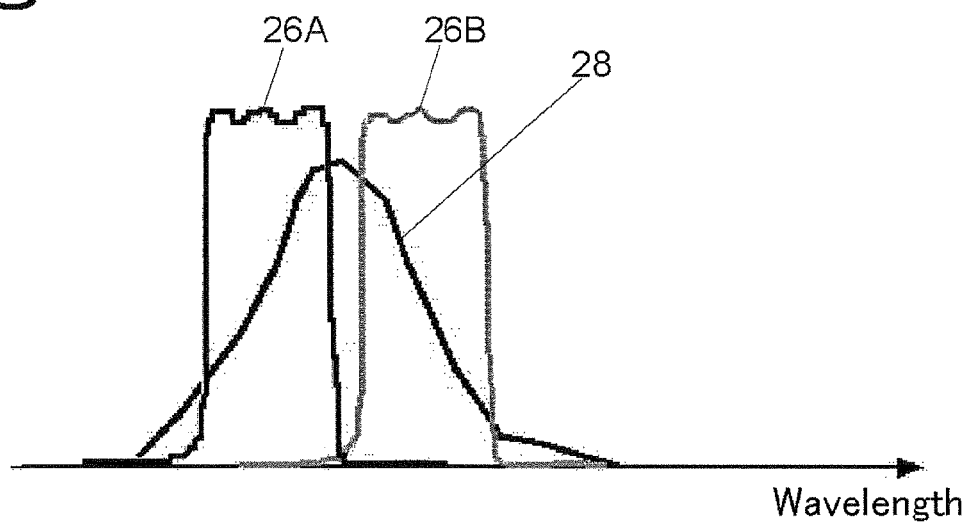

FLUORESCENT MEASUREMENT DEVICE FOR LIVING BODY AND EXCITING LIGHT-IRRADIATING DEVICE FOR FLUORESCENT MEASUREMENT

TECHNICAL FIELD

The present invention relates to an optical bioimaging technique for small animals.

BACKGROUND ART

A technique for imaging the distribution of molecular species in a living body is an important tool used in medical and biological research. Imaging of molecular species at the cellular level has been widely performed using a microscope and a molecular probe such as a molecular probe labeled with a fluorescence pigment or a chemiluminescence molecular probe. However, recently, there is a growing demand for devices for observing in vivo the distribution of molecular species of interest at the organ or whole-body level rather than the cellular level. For example, such an observation device allows the imaging of the distribution of target cancer cells labeled with a fluorescence probe in the body of a small living animal, such as a mouse, to monitor the growth of the target cancer cells over a fixed period of time, such as every day or every week. In a case where the growth of cancer cells in the body of an animal is monitored using a conventional device for cellular-level imaging, the animal is killed to stain or fluorescently-label cancer cells in a predetermined part of the body of the animal. In this case, the growth of cancer cells in the same individual cannot be monitored over a long period of time. For this reason, there is a demand for the development of a device capable of observing the distribution of molecular species in the body of a small living animal to obtain internal information about the body of the small animal.

As an exciting light-irradiating device for exciting fluorescence, one shown in FIG. 9 is known. As shown in FIG. 9, the exciting light-irradiating device has a filter wheel 8 and a multi-branched optical fiber bundle 16 to irradiate an object with light having a wavelength selected by the filter wheel 8 and the multi-branched optical fiber bundle 16. More specifically, light is emitted from a light source 2 such as a tungsten halogen lamp, collected by a lens 4 so as to enter an optical guide 6, and guided to a filter 10 mounted on the filter wheel 8 by the optical guide 6 so that only light passed through the filter 10 is guided to an entrance portion 16A of the multi-branched optical fiber bundle 16. Optical fibers constituting the multi-branched optical fiber bundle 16 are tied in a bundle at the entrance portion 16A, and are separated into four bundles at the position of a ring 16B provided on the way to a dark measurement chamber (not shown). The distal ends of these four optical fiber bundles are placed in the dark measurement chamber. The filter wheel 8 has a plurality of filters, and a desired excitation wavelength is selected by switching among these filters. Exciting light is guided by the multi-branched optical fiber bundle 16 to predetermined positions in the dark measurement chamber for measuring fluorescence. A device similar to the exciting light-irradiating device shown in FIG. 9 is also disclosed in U.S. Pat. No. 6,894,289.

DISCLOSURE OF THE INVENTION

Problem to be Solved by the Invention

Near-infrared light with wavelengths of about 650 to 900 nm can relatively easily pass through a living body. Therefore, a technique is widely used to obtain information about molecules or tissues of interest within a small animal, which is performed by allowing a fluorescence probe to be selectively bound to molecules of interest, such as tumor tissues, within a small animal and then observing fluorescence from the outside of the small animal. In this case, light for exciting fluorescence and a fluorescence image measuring method preferably satisfy the following requirements.

1) The fundamental principle, on which fluorescence measurement is based, is that light emitted from fluorescent molecules of interest by irradiating a sample with exciting light has a wavelength different from that of the exciting light and, therefore, only wavelength components of fluorescence can be detected with very high sensitivity by providing a filter, which completely blocks wavelength components of the exciting light, on the detection side. However, in actuality, the spectrum of exciting light often slightly contains components of weak light (stray light) which have the same wavelengths as components of fluorescence to be detected. These components become leak light and overlap with fluorescence to be detected, thereby lowering detection limits. Therefore, it is necessary to take measures to eliminate wavelength components, which will become leak light and overlap with wavelength components of light to be detected, from wavelength components of exciting light as much as possible.

2) The irradiation direction of exciting light is preferably switchable because obtainable information is different depending on whether a sample is irradiated with exciting light from the front, back, or lateral side of the sample (which will be described later with reference to some embodiments).

3) The wavelength of exciting light is different depending on the kind of pigment (fluorescent molecule) used as a probe, and is therefore preferably switchable easily.

4) Further, it is preferred that a sample is observed not only from one direction but also from multiple directions to pick up fluorescence images of the sample. In this case, it is necessary to arrange a plurality of exciting light sources in a limited space within a dark measurement chamber to irradiate the sample with exciting light from various angles (positions). Therefore, the size of an exciting light-irradiating device is preferably as small as possible while the exciting light-irradiating device has the above-described functions 1), 2), and 3).

In the case of the exciting light-irradiating device shown in FIG. 9, the wavelength of exciting light is selected by allowing light, which is emitted from a white light source 2 such as a halogen lamp and has a variety of wavelength components, to pass through the filter 10 selected by rotating the filter wheel 8, and the exciting light is guided to predetermined positions in a measurement chamber by the optical fiber bundle 16. As the optical fiber bundle 16, a multi-branched optical fiber bundle 16 (in this case, a four-branched optical fiber bundle) is used to guide exciting light to desired positions. However, the exciting light-irradiating device of this type cannot satisfy all the above-described requirements 1) to 4). For example, the excitation wavelength can be changed by switching among the filters 10, but the irradiation direction of the exciting light cannot be selected because the exciting light is guided by all the multi-branched optical fiber bundle 16 at the same time. Further, such an exciting light-irradiating device has, of course, a large size and a complicated structure because switching among the filters 10 is mechanically performed. Further, as will be described later, the use of optical fibers is disadvantageous from the viewpoint of reducing wavelength components that will become leak light.

Conventional fluorescence measurement for a living body is widely performed using a fluorescence microscope. In this case, exciting light is usually guided from the outside of a microscope to a measurement unit of the microscope with the use of an optical system or an optical fiber. On the other hand, unlike the case of fluorescent measurement using a fluorescence microscope, in the case of macroscopic measurement of a small animal, a sample is large, and therefore, directly arranging an exciting light-irradiating device in a measurement chamber is more advantageous than guiding exciting light from the outside. In order to directly arrange an exciting light-irradiating device in a measurement chamber, it is necessary to reduce the size of the exciting light-irradiating device. Further, as will be described later, it has been found that not only switching of an excitation wavelength but also switching of an excitation direction or multidirectional observation is effective for fluorescence measurement. Also from the viewpoint of switching of an excitation direction or multidirectional observation, reduction in the size of an exciting light-irradiating device is an issue to be resolved.

In view of the above requirements, it is a first object of the present invention to provide a fluorescence measurement device for a living body which satisfies at least the above requirements 1) and 2), can reduce wavelength components that will become leak light, and is capable of easily switching the irradiation direction of exciting light.

It is a second object of the present invention to provide an exciting light-irradiating device which satisfies the above requirement 4), that is, which has a reduced size to be directly arranged in the fluorescence measurement device for a living body so that a sample can be irradiated with exciting light without optical fibers.

Means for Solving the Problem

Instead of a tungsten light source which emits light over a wide wavelength range, a laser diode (LD: semiconductor laser) or a light-emitting diode (LED) which emits light with a substantially single wavelength is used as a light source. In addition, such an LD or an LED is used together with a filter having an optical property to eliminate disturbing wavelength components overlapping with wavelength components of fluorescence to be detected from wavelength components of exciting light emitted from the LD or LED. Further, a light excitation unit is formed by arranging these light sources at mutually different positions or side-by-side. This makes it possible to satisfy the above-described requirements 1) and 2) or 3) because the irradiation direction of exciting light can be selected simply by turning on only a desired light source of the light excitation unit.

That is, the fluorescence measurement device for a living body according to the present invention comprises: a sample holder on which a living body sample is to be placed; an exciting light-irradiating device having a plurality of exciting light sources placed at mutually different positions; an electrical switch for controlling lighting of the exciting light sources; a fluorescence filter allowing only a predetermined wavelength component of fluorescence emitted from the sample placed on the sample holder to pass through; a detector for picking up a fluorescence image produced by fluorescence passed through the fluorescence filter; and an image display device for displaying an image picked up by the detector, wherein each of the exciting light sources of the exciting light-irradiating device has an optical filter for eliminating, from exciting light emitted from the exciting light source, at least a wavelength component having a wavelength that is the same as that allowed to pass through the fluorescence filter.

Here, in the exciting light-irradiating device, the phrase "arranged at mutually different positions" means not only a case where the exciting light sources are arranged separately from each other but also a case where the exciting light sources are arranged side-by-side.

It is generally assumed that an LD emits light with a single wavelength and, therefore, it is not necessary to use a filter together with the LD. However, looking at the emission spectrum of an LD in detail, as shown in FIG. 1A, there is a weak and broad emission part 22 around a strong oscillation line 20. This weak and broad emission part 22 extends to a long-wavelength range, and, therefore, a part of the weak and broad emission part 22, 22A, overlaps with a passband 24 of a fluorescence filter for detecting fluorescence. In this case, leak light passed through the fluorescence filter becomes background light. Therefore, an excitation filter having a narrow passband 26 including a wavelength range of the strong oscillation line 20 is used together with the LD to eliminate leak light to achieve measurements under low background conditions. Also in the case of an emission spectrum 28 of an LED, as shown in FIG. 1B, a tail 28A of the emission spectrum 28 on the long-wavelength side of the emission wavelength range of the LED often overlaps with the passband 24 of a fluorescence filter. Therefore, also in the case of using an LED as a light source, the undesired tail on the long-wavelength side is eliminated by using an appropriately-designed excitation filter together with the LED. This makes it possible to eliminate wavelength components that will become leak light from exciting light to achieve measurements under low background conditions. In this regard, as the details will be described below, there is a large difference in the ability to reduce leakage wavelength components between the present invention and a conventional method shown in FIG. 9 in which the wavelength of white light is selected by switching among filters. In general, the ability of the filter 26 to prevent wavelength components that should be blocked (the part of 22A or 28A) from passing through is not perfect, and the filter 26 typically allows light with an intensity of about $10^{-6}$ (i.e., 0.0001%) of that of incident light to pass through. Therefore, in a case where the wavelength of white light as exciting light is selected by a blocking filter that is the same as the filter 26, leak light with an intensity of about $10^{-6}$ of that of incident light is produced. On the other hand, in a case where an LD or an LED is used as a light source, the intensity of part of 22A in FIG. 1A or 28A in FIG. 1B is originally smaller by 2 to 3 orders magnitude than that of the main component 20 or 28 of exciting light appearing at the center of the spectrum. Therefore, in a case where such an LD or an LED is used together with a blocking filter allowing light with an intensity of about $10^{-6}$ of that of incident light to pass through, the intensity of wavelength components that will become leak light becomes $10^{-8}$ to $10^{-9}$ of that of the main component of exciting light. This is equal to the result obtained by using a higher-performance filter. As described above, the present invention has the effect of allowing an exciting light source to be easily selected and, in addition, is also very advantageous in the ability of improving fluorescence detectability by reducing leakage wavelength components. Further, it can be emphasized that the present invention does not use optical fibers nor a filter wheel, which has the following two advantages from the viewpoint of reducing wavelength components that will become leak light. One is that fluorescence/Raman light emitted from optical fibers can be eliminated. If optical fibers are used, the optical fibers are required to have a length of about 1 m, and therefore, fluorescence/Raman light emitted from a fiber material cannot be ignored in some cases. The other is that a filter is fixed to a light source by a simple and cheap method, and therefore, leakage of light never occurs. If a filter wheel is used, it is absolutely necessary to keep a space around the filter wheel to move it, and therefore, light is likely to leak from the space. In this case, it is necessary to perform complicated machining with high accuracy to prevent leakage of light.

The above-described factors contributing to a reduction in wavelength components that will become leak light can be summarized in the following three points: 1) the blocking efficiency of a filter can be substantially improved by using together a filter and a light source whose emission intensity in a wavelength range that should be blocked by the filter is weak; 2) there is no emission of light from optical fibers; and 3) leakage of light from a space necessary for a movable part such as a filter wheel never occurs.

In order to achieve the requirement 3); that is the requirement for more easy switching of an excitation wavelength depending on the kind of pigment used as a probe, it is preferred that the plurality of exciting light sources have mutually different emission wavelengths and are each combined with a filter so that the wavelength of exciting light can be switched by ON/OFF switching of the exciting light sources by the electrical switch. However, in some cases, as shown in FIG. 1C, it is possible to use a variant composed of the plurality of exciting light sources having the same wavelength distribution. More specifically, the variant uses an exciting light source obtained by combining a light-emitting diode having wavelength characteristics 28 and an excitation filter 26A, and an exciting light source obtained by combining another light-emitting diode having the same wavelength characteristics 28 and an excitation filter 26B. In this case, the main wavelength component of exciting light is determined by the filter. Therefore, although these light sources have the same wavelength characteristics, when one of the two exciting light sources using the filter 26A is lighted up, wavelengths that can pass through the filter 26A are emitted and when the other exciting light source using the filter 26B is lighted up, wavelengths that can pass through the filter 26B are emitted. However, in this case, since the emission spectrum of the exciting light source is strong outside the passband of the filter 26A, it cannot be expected that the first factor of the above-described three factors contributing to a reduction in wavelength components that will become leak light will be satisfied, but it can be expected that the second and third factors will be satisfied. Therefore, this variant is still effective as an alternative when an exciting light source that is suitable for the filter 26A cannot be obtained. One thing that can be said from the variant shown in FIG. 1C is that a substantial irradiation wavelength is determined by the spectrum of the product of the emission spectrum of a light source and the transmission spectrum of a filter. Therefore, as shown in FIG. 1C, when the width of the transmission spectrum of the filter is narrower than that of the spectrum of the light source, an irradiation wavelength is determined depending on the difference in transmission spectrum between the filters. On the other hand, which of the filters is allowed to function is controlled by ON/OFF switching of the light sources. That is, a desired excitation wavelength can be selected not by mechanically moving a filter but by ON/OFF switching of the light sources having the same wavelength characteristics (or mutually independent wavelength characteristics).

In order to obtain images of a sample observed from multiple directions covering 360° around the sample, it is preferred that the detector is a two-dimensional detector and that the fluorescence measurement device further includes a light guiding optical system, such as a reflector, for guiding images produced by fluorescence emitted in various observation directions from the sample placed on the sample holder. By using such a multidirectional observation device, it is possible to prevent from missing a tumor even when the tumor is developed in the back side of a small animal. Further, it is also possible to obtain information about the depth of a fluorescent material present in a sample animal by multidirectional lighting, which will be described later in examples.

In the case of a conventional exciting light-irradiating device widely used such as one shown in FIG. 9, a tungsten halogen lamp is used as a light source, a desired excitation wavelength is selected by switching among excitation filters, and exciting light is delivered to predetermined locations in a measurement chamber by a branched optical fiber bundle. In this case, however, light is guided by all of the branched optical fibers at the same time, and therefore it is impossible to deliver light only to a desired location. Further, it is necessary to use expensive optical fibers which emit no fluorescence. This is because, as described above, fluorescence emitted from optical fibers themselves is also a factor responsible for generating wavelength components that will become leak light. On the other hand, a small LD or LED is a space-saving light source, and therefore, by placing the LD or LED within the fluorescence measurement device for a living body, it is possible to eliminate the necessity to use optical fibers, thereby satisfying the requirement 4).

The exciting light-irradiating device for fluorescence measurement according to the present invention made for the object is an exciting light-irradiating device for fluorescence measurement to be placed in a fluorescence measurement device for a living body for picking up a fluorescence image produced by fluorescence passed through a fluorescence filter allowing only a predetermined wavelength component of fluorescence emitted from a sample irradiated with exciting light to pass through, the exciting light-irradiating device comprises: an irradiating unit having an exciting light source composed of a laser diode or a light-emitting diode and a filter integrally provided with the exciting light source and having an optical property to eliminate at least the predetermined wavelength component from a spectrum of the exciting light source; and an electrical switch for controlling lighting of the exciting light source.

It is preferred that the number of the irradiating units is two or more, wherein these irradiating units are placed in different irradiation directions, and the two or more irradiating units different in emission wavelength are placed in each of the irradiation directions. This makes it possible to select an excitation wavelength and an irradiation direction by turning on the exciting light source of a desired one of the irradiating units.

The irradiating unit may have a plurality of pairs of the exciting light source and the filter. In this case, it is preferred that the exciting light sources are mutually different in emission wavelength and that switching between/among the exciting light sources different in emission wavelength can be performed by the electrical switch.

In order to allow the filter to maintain its optical characteristics, it is preferred that a collimator lens or an aperture is provided between the exciting light source and the filter as a means for limiting the divergence angle of light emitted from the exciting light source to allow the exciting light to enter the filter and that a diverging lens for diverging light passed through the filter is provided on the exit side of the filter.

Further, the irradiating unit may be detachably attached to a holder provided in the fluorescence measurement device.

As has been described above, the four requirements of a light source for exciting fluorescence for use in fluorescence measurement of macro-size samples can be satisfied by the above-described methods. The point of these methods is again summarized as follows.

The point is that the present inventors have focused attention on the fact that a sample is a macro-size sample, and therefore, there is enough space to perform switching between/among light sources for irradiating fluorescence by ON/OFF switching of the light sources arranged side-by-side. In the case of conventional fluorescence measurement of microscopically small samples, a rotary filter disk is usually used to physically exchange the wavelength filter because it is necessary to perform switching of a light source or a filter in the same location. On the other hand, the present invention effectively utilizes that a sample is a macro-size sample, which makes it possible to remove constrains resulting from that a sample is microscopically small. Therefore, the present invention proposes a method by which switching of a wavelength and an irradiation direction can be performed simply by electrical ON/OFF switching of different irradiating light sources, each of which is obtained by integrally combining a light source and a filter, arranged side-by-side without any mechanical driving.

Based on this idea, the present inventors have invented an integrated combination of a light-emitting diode or a laser diode as a light source, which has a small light spot area and a small physical size, and is therefore advantageous for "integrally combining a light source and a filter", and a filter cut into small blocks.

As a result, it is possible to satisfy the four requirements having been described at the beginning: 1) to satisfy three factors contributing to a reduction in wavelength components that will become leak light (improvement in blocking efficiency of a filter, no emission of light such as fluorescence from optical fibers, and no leakage of light from a gap created by a mechanically movable part), 2) to facilitate switching of an irradiation direction, 3) to perform switching of a wavelength by ON/OFF switching of light sources, and 4) to reduce the size of an irradiating device.

Effects of the Invention

Since the exciting light-irradiating device according to the present invention has a light source constituted from a laser diode or a light-emitting diode and further uses a filter for eliminating leak light together with the light source, the fluorescence measurement device for a living body can detect only the components of fluorescence with very high sensitivity under low stray-light conditions. Further, a laser diode or a light-emitting diode does not emit light in an unnecessary wavelength range, and the intensity of light emitted from a laser diode or a light-emitting diode per unit wavelength interval is great. Therefore, as compared to a case where the wavelength of exciting light is selected by allowing light emitted from a halogen lamp to pass through a desired one of filters mounted on a filter wheel, stronger exciting light can be obtained, which contributes to a reduction in measurement time and an improvement in measurement sensitivity.

Further, since the fluorescence measurement device for a living body according to the present invention is configured to control the lighting of a plurality of exciting light sources arranged at different positions, the irradiation direction of exciting light can be freely selected without using any mechanical system (e.g., the irradiation direction of exciting light can be switched or a sample can be irradiated with exciting light from two or more directions at the same time). This makes it possible to obtain new findings about locations where fluorescent molecules to be detected are present.

The irradiating unit of the exciting light-irradiating device according to the present invention is an assembly whose size is small enough to be placed in the fluorescence measurement device, and therefore can directly irradiate a sample to excite fluorescence without using an optical guide element such as optical fibers.

Further, the use of such a downsized exciting light source makes it possible to satisfy the need for arranging a plurality of light sources without using optical fibers in locations where space is limited by, for example, a reflector to perform multidirectional observation.

BRIEF DESCRIPTION OF THE DRAWINGS

FIG. 1C is a drawing showing the spectrum of an exciting light source including two light-emitting diodes having the same wavelength characteristics and two excitation filters different in transmission characteristics combined with the light-emitting diodes, respectively.

FIGS. 8B1 to 8B5 are images taken by a simultaneous five-direction observation device equipped with a five-direction switchable irradiating device.

Figure 1A:
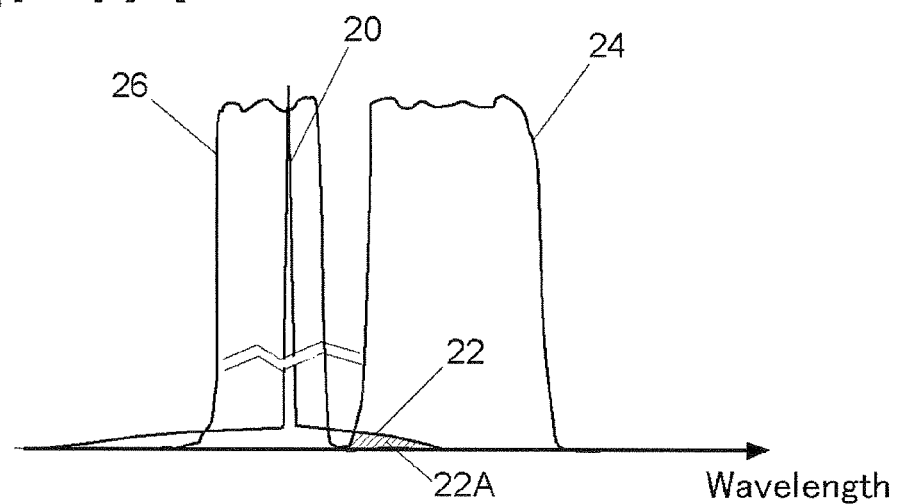
FIG. 1A is a drawing showing the emission spectrum of a laser diode and the transmission characteristics of a filter.

DESCRIPTION OF THE REFERENCE NUMERALS 30, 32, 34, 42, 48 irradiating unit
36 camera unit
$F_{EM}$ fluorescence filter
$F_{ex}$ excitation filter
L imaging lens
38 CCD detector
40 measurement chamber

DETAILED DESCRIPTION OF THE INVENTION (First Embodiment)
<Fluorescence Observation Device Configured to be Able to Switch Among Three Irradiation Directions, Left, Right, and Back>

Figure 2:
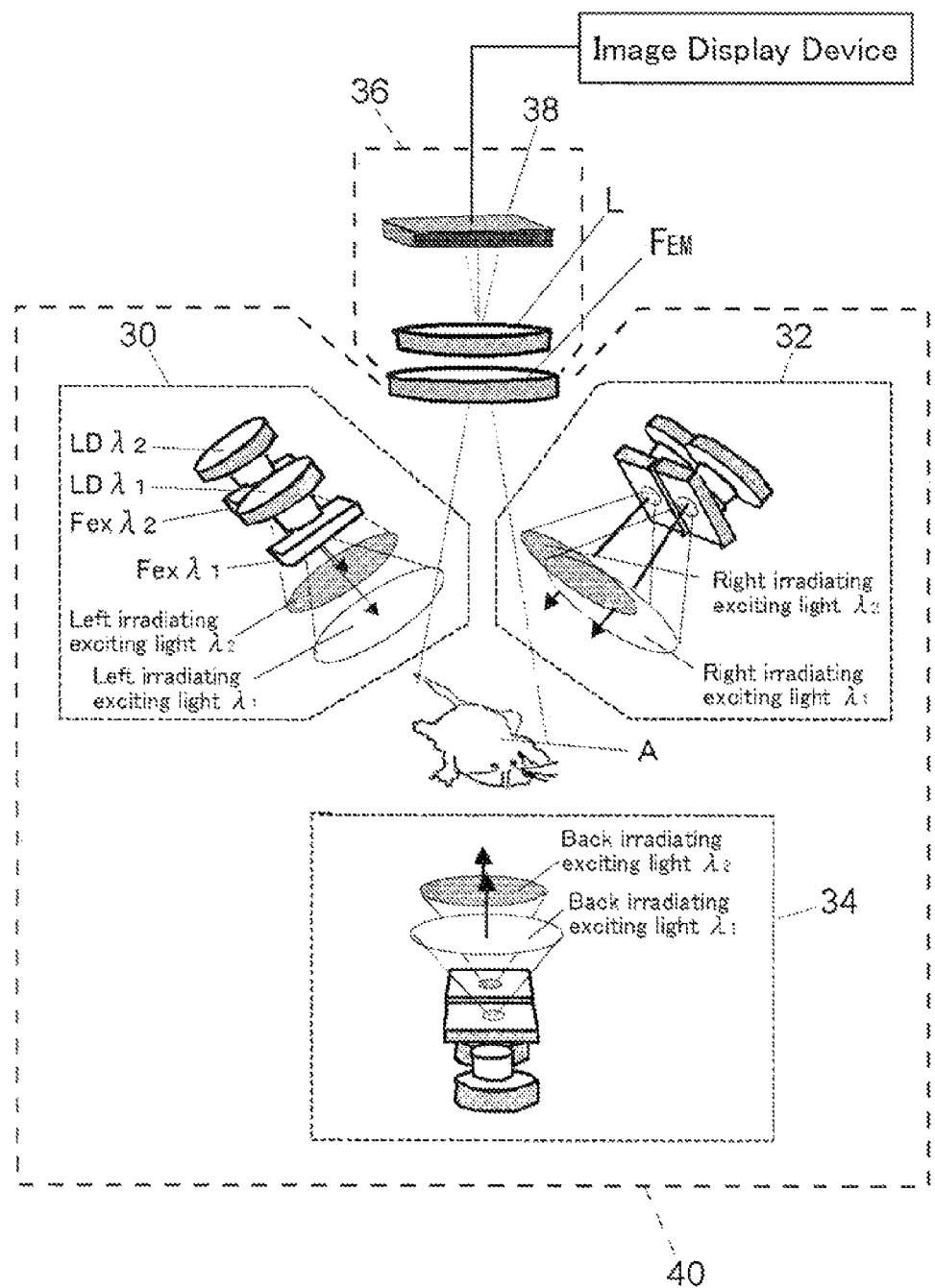
FIG. 2 is a schematic perspective view of a main part of one embodiment of a fluorescence measurement device for a living body.

FIG. 2 shows a fluorescence observation device according to a first embodiment configured to be able to switch among three irradiation directions, left, right, and back. A sample holder (not shown) is provided in the center of the fluorescence observation device, and a small animal is placed as a living body sample A on the sample holder. Further, irradiating units for exciting fluorescence (i.e., a left-side irradiating unit 30, a right-side irradiating unit 32, a back-side irradiating unit 34) are placed in three positions around the living body sample A. Fluorescence emitted from the sample A enters a camera unit 36, passes through a fluorescence filter $F_{EM}$, and is formed into an image by an imaging lens L on a CCD detector 38 as a two-dimensional detector so that a fluorescence image is obtained.

Figure 9:
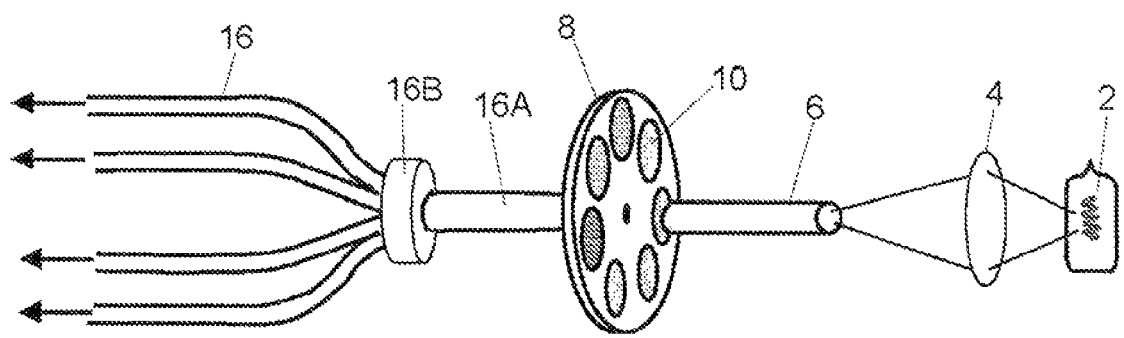
FIG. 9 is a schematic perspective view of a conventional exciting light-irradiating device.

The irradiating units 30, 32, and 34 placed in three positions are the same, and therefore, the elements of the left-side irradiating unit 30 shown in FIG. 2 will be described. The irradiating unit 30 has two laser diodes LDλ1 and LDλ22 that emit light with a wavelength of λ1 and light with a wavelength of λ2, respectively. Excitation filters Fexλ1 and Fexλ2 are attached to the laser diodes LDλ1 and LDλ2, respectively. The filter Fexλ1 eliminates disturbing wavelength components overlapping with the wavelength components of light to be detected from the emission spectrum of the laser diode LDλ1. Therefore, left irradiating exciting light λ1 can be obtained, which contains few wavelength components that will become leak light. This is because the irradiating unit 30 satisfies the above-described three factors contributing to a reduction in wavelength components that will become leak light. Similarly, light emitted from the laser diode LDλ2 passes through the excitation filter Fexλ2 so that left-side irradiating exciting light λ2 can be obtained. Switching between the left-side irradiating exciting light λ1 and the left-side irradiating exciting light λ2 is performed simply by ON/OFF switching of the laser diodes LDλ1 and LDλ2. Since the excitation filters Fexλ1 and LDλ2 are fixed to the laser diodes LDλ1 and LDλ2, respectively, and therefore, it is not necessary to use a mechanical switching means such as a conventional filter wheel shown in FIG. 9.

Since the right-side irradiating unit 32 and the back-side irradiating unit 34 have exactly the same structure as the left-side irradiating unit 30, the fluorescence observation device according to the first embodiment has six laser diodes in total, and can select an excitation wavelength from two different wavelengths combined with three irradiating directions. Therefore, a combination of an excitation wavelength and an irradiation direction can be selected at the same time without using a mechanical driving unit by turning on a desired one of the six laser diodes. CCD images of three-times exposure for the sample A irradiated respectively from three different directions can be obtained per excitation wavelength. Useful findings can be obtained from the difference among these fluorescence images resulting from the difference in irradiation direction, which will be described in detail later with reference to a measurement example using a phantom shown in FIG. 8.

Further, two or more of these laser diodes may be turned on at the same time. For example, "concurrent irradiation from three directions" or "concurrent irradiation from the left and right sides" may be performed to obtain rough information in a short period of time.

In FIG. 2, an area enclosed with a broken line indicated by a reference numeral 40 represents a dark measurement chamber that shuts out external light. As described above, each of the left-side irradiating unit 30, the right-side irradiating unit 32, and the back-side irradiating unit 34 has all the elements including light sources and filters, and all of the three irradiating units are placed in the measurement chamber 40. This is a fundamental difference between the fluorescence measurement device according to the present invention and a conventional system shown in FIG. 9, in which light is introduced into a measurement chamber from the outside using optical fibers, or a system for use in fluorescence microscope observation, in which light is guided to the position of a sample by a lens or a reflector.

In the upper part of FIG. 2, another area enclosed with a broken line is also shown, which represents a camera unit 36. The measurement chamber 40 and the camera unit 36 are separated from each other by the fluorescence filter $F_{EM}$. Therefore, components of scattering light emitted from the sample A other than components of fluorescence are blocked by the fluorescence filter $F_{EM}$. As a result, only the components passed through the fluorescence filter $F_{EM}$ are introduced into the camera unit 36 and detected. It is to be noted that in FIG. 2, only one fluorescence filter $F_{EM}$ is shown for simplicity of illustration, but in actuality, a rotary filter disk is located so that switching between/among filters can be performed. Therefore, when the wavelength of exciting light emitted from the irradiating unit 30, 32, or 34 is changed, the rotary filter disk (not shown) is rotated to select an appropriate fluorescence filter $F_{EM}$ before measurement.

<Example of Irradiating Unit Having Increased Number of Light Sources>

Figure 3:
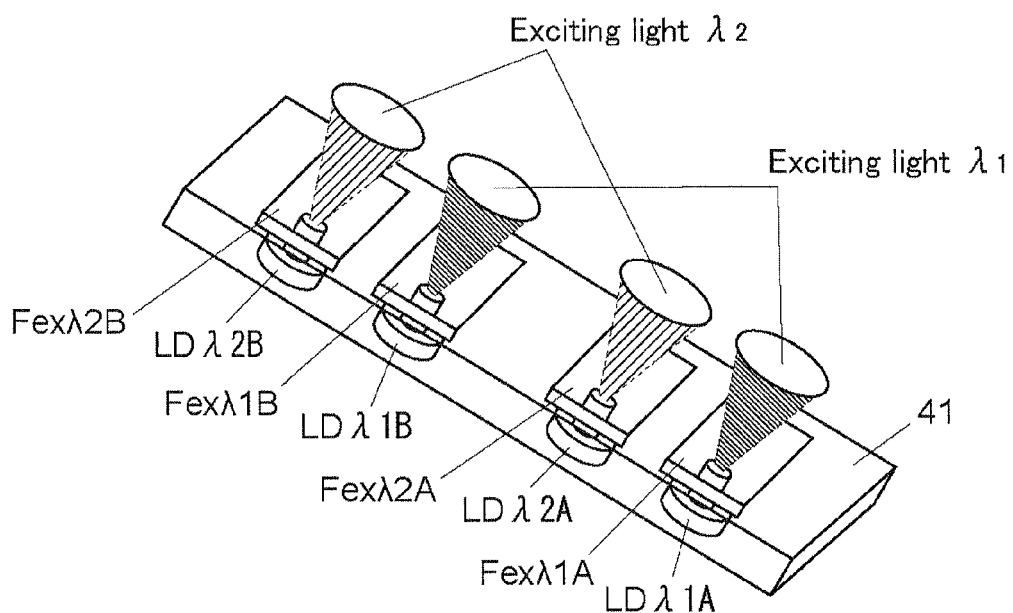
FIG. 3 is a schematic perspective view of one embodiment of an exciting light-irradiating device.

Each of the irradiating units shown in FIG. 2 may be changed to another irradiating unit having an increased number of light sources shown in FIG. 3 to irradiate the sample A from three different directions. The irradiating unit shown in FIG. 3 uses two laser diodes per wavelength, and therefore, a relatively large sample can be irradiated with exciting light more uniformly by turning on the two laser diodes at the same time.

More specifically, the irradiating unit shown in FIG. 3 has a structure in which four laser diodes LDλ1A, LDλ2A, LDλ1B, and LDλ2B are mounted on a light source mounting base 40. The light source mounting base 41 is a plate-shaped holder extending in a direction parallel to the body axis of a small animal, and the four laser diodes are arranged in a direction parallel to the body axis of the small animal. In this irradiating unit shown in FIG. 3, two of the four laser diodes, that is, the laser diodes LDλ1A and LDλ1B emit light of the same wavelength (e.g., 780 nm), and the other two laser diodes, that is, the laser diodes LDλ2A and LDλ2B emit light of another wavelength (e.g., 690 nm).

Further, excitation filters Fexλ1A, Fexλ2A, Fexλ1B, and Fexλ2B are attached to the four laser diodes, respectively, and therefore, four pairs of a laser diode and an excitation filter (i.e., a pair of LDλ1A and Fexλ1A, a pair of LDλ2A and Fexλ2A, a pair of LDλ1B and Fexλ1B, and a pair of LDλ2B and Fexλ2B) each emit exciting light toward the sample A. As has been described above, the emission spectrum of a laser diode often has weak emission components in the foot thereof around its oscillation wavelength. However, the present inventors have found that a combination use of a laser diode and a filter suitable for the laser diode has the effect of reducing disturbing wavelength components (stray-light), which are contained in exciting light and overlap with wavelength components of fluorescence to be detected, to very low levels. When the irradiating units having such a structure as described above are arranged around a sample, an irradiation direction and an excitation wavelength can be freely selected simply by electrically selecting (turning on) one or two of the four laser diodes of a desired one of the three irradiating units.

It is to be noted that the example shown in FIG. 3 has laser diodes of two different wavelengths, but as a matter of course, laser diodes of three or more different wavelengths may be arranged as space permits.

Further, the laser diode and the excitation light filter are mechanically fixed to each other. Therefore, it is very easy to design an appropriate mechanical light shield (not shown) that prevent the occurrence of light leakage through a gap between the laser diode and the filter, at the same time ensuring the necessary light emitted from the laser diode always pass through the filter.

When the excitation-side of the fluorescence observation device has such a structure as described above, an excitation wavelength and a fluorescence wavelength can be selected in the following manner. The position of an exciting light source and the wavelength of exciting light are selected by electrical ON/OFF switching, and the fluorescence filter $F_{EM}$ shown in FIG. 2 is selected by switching between/among two or more filters $F_{EM}$ different in passband mounted on a rotary disk by rotating the rotary disk. In this case, only a mechanism for rotating the rotary disk having fluorescence filters $F_{EM}$ remains as a mechanically movable part, but there are no other movable parts. Therefore, a very simple switching method can be achieved as a method for exciting and detecting fluorescence from multiple directions.

<Example of Irradiating Unit Having Plurality of Light Emitters Arranged in Mosaic Fashion>

Figure 4A:
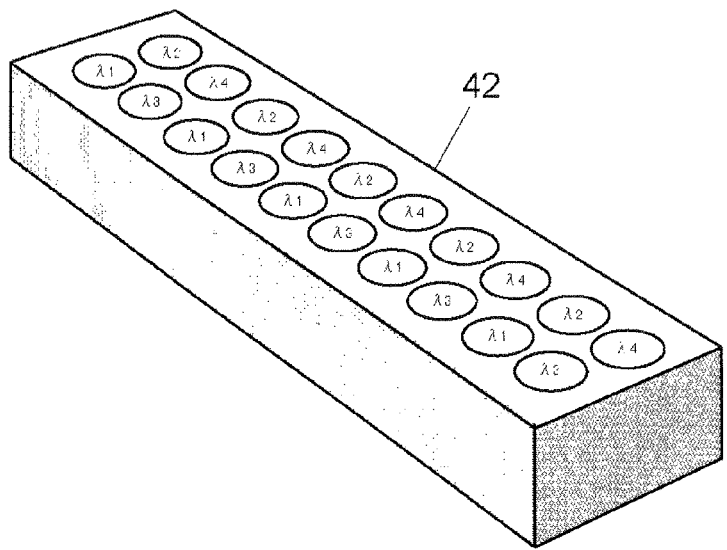
FIG. 4A is a perspective view showing the appearance of another embodiment of an exciting light-irradiating device.
Figure 4B:
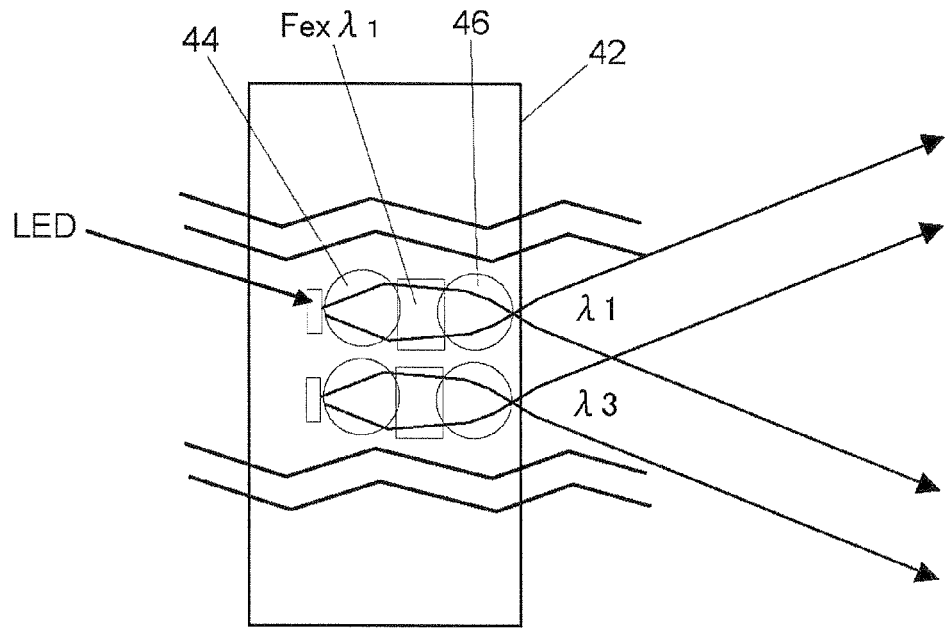
FIG. 4B is a sectional view of the exciting light-irradiating device shown in FIG. 4A.

As shown in FIGS. 4A and 4B, the irradiating unit may be formed as a planar multiple-wavelength exciting light source having a plurality of pairs of a light emitter and an excitation filter $F_{ex}$ arranged in mosaic fashion. FIG. 4A shows a rectangular irradiating unit 42 in which four wavelengths $\lambda 1$, $\lambda 2$, $\lambda 3$, and $\lambda 4$ are arranged repeatedly. Such a planar irradiating unit 42 is suitable for uniform irradiation of a relatively large sample.

Figure 1B:
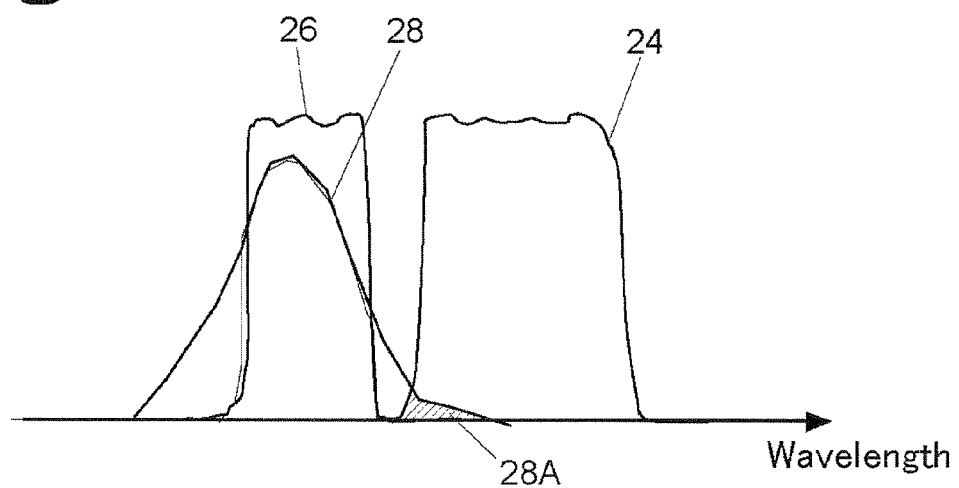
FIG. 1B is a drawing showing the emission spectrum of a light-emitting diode and the transmission characteristics of a filter.

FIG. 4B shows the structure of the inside of the irradiating unit 42. The irradiating unit 42 has a plurality of cheap LEDs as light emitters, and each of the LEDs is combined with a small excitation filter $F_{ex}$. The emission spectrum of the LED is broad, but as shown in FIG. 1B, leak light (stray light) can be reduced by eliminating the emission spectrum of the LED overlapping with the emission wavelength of fluorescence with the use of the excitation filter $F_{ex}$ constituted from an interference filter.

In a case where light emitted from the LED enters the excitation filter $F_{ex}$ very obliquely (i.e., the angle of divergence of light emitted from the LED is too large to allow the interference filter to exhibit its inherent performance), as shown in FIG. 4B, the excitation filter $F_{ex}$ is preferably sandwiched between a collimator lens 44 and a diverging lens 46 to prevent the deterioration of performance of the interference filter. In this example, diverging light emitted from the small LED device is allowed to pass through a collimator lens 44 constituted from a convex lens such as a sphere lens to reduce the angle of divergence of the diverging light, and then the light is allowed to pass through the interference filter $F_{ex}$ and then through the diverging lens 46 to again increase the angle of divergence of the scattering light to illuminate a wide range. It is to be noted that the angle of divergence of the light emitted from the LED may be reduced by an appropriate aperture instead of the collimator lens 44. This is because when most of the light emitted from a light source such as a laser diode is concentrated within a small angle, the loss of light quantity is within the allowable range even when an aperture is used. Further, the diverging lens may be either a convex lens such as a sphere lens shown in FIG. 4B or a concave lens. It is to be noted that the procedure for collimating or diverging before and after the filter $F_{ex}$, respectively can be, of course, also applied to the irradiating unit shown in FIG. 2 or FIG. 3, but is not described for the sake of simplicity of explanation and illustration.

The fluorescence imaging device shown in FIG. 2 configured to be able to switch among three irradiation directions can be obtained by arranging the irradiating units shown in FIG. 2, 3, 4A, or 4B having such a structure as described above in as many as the number of irradiation directions (in the first embodiment, three irradiating units).

Figure 4C:
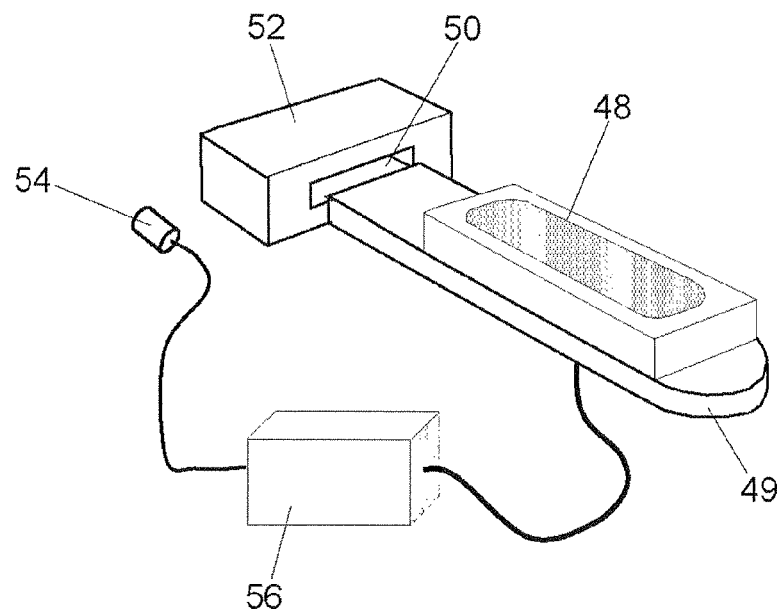
FIG. 4C is a perspective view showing the appearance of yet another embodiment of an exciting light-irradiating device.

FIG. 4C shows yet another example of the irradiating unit. An irradiating unit 48 shown in FIG. 4C is not fixed to a main body of the fluorescence measurement device but is detachably attached to the main body of the fluorescence measurement device. More specifically, the irradiating unit 48 is fixed to an appropriate detachable holder 49, and the detachable holder 49 is inserted into a slot 50 provided in a holder 52 attached to the main body of the fluorescence measurement device. In this way, the irradiating unit 48 is detachably attached to the main body of the fluorescence measurement device. Electrical power is supplied from a socket 54 via a switch box 56 to the irradiating unit 48. The irradiating unit 48 is ON/OFF controlled by operating the switch box 56.

Since the irradiating unit 48 has such a structure as described above, even when the irradiating unit 48 can emit only one wavelength of light, any wavelength can be selected by replacing it with the irradiating unit 48 that emits a different wavelength of light. Further, a different type of irradiating unit can also be used by attaching it to the fluorescence measurement device.

An appropriate switching circuit may be provided for the irradiating unit 48, which makes it possible to allow the irradiating unit 48 to emit light only in case of necessity. Further, selection of an irradiation direction also becomes possible by attaching the holders 52, into which the irradiating units 48 are to be inserted, to the main body of the fluorescence measurement device at different positions so that a sample can be irradiated with light from various angles. The detachable irradiating unit 48 may be configured to have two or more emission wavelengths so that an emission wavelength can be switched by ON/OFF switching of lighting.

It is to be noted that in this example, the irradiating unit 48 is detachably attached to the fluorescence measurement device by inserting the detachable holder 49 into the slot 50, but this is merely an example. It goes without saying that the irradiating unit 48 may be detachably attached to the holder 52 by an appropriate holding method.

(Second Embodiment)

The fluorescence measurement device according to the first embodiment is configured to be able to irradiate a living body sample, which is observed from one direction, with light from multiple directions. On the other hand, a fluorescence measurement device according to a second embodiment is a combination of a multidirectional observation device and a multidirectional irradiating unit. Prior to the description of the fluorescence measurement device according to the second embodiment, a multidirectional observation-type fluorescence measurement device will be first described, and then a method for combining the multidirectional observation-type fluorescence measurement device and a multidirectional irradiating unit will be described.

<Multidirectional Observation-Type Fluorescence Measurement Device>

Multidirectional observation is necessary to, for example, prevent from missing a tumor developing in the back side of an observation direction. Therefore, it is necessary to observe a sample from multiple directions, e.g., front, back, left, right, etc. As a method advantageous to perform multidirectional observation, a method shown in FIG. 5 can be mentioned. In this case, a sample A is observed from five directions at the same time using a two-dimensional detector 38 composed of a CCD detector, and images of the sample A observed from five directions are formed on the common two-dimensional detector 38 with the use of a multi-mirror assembly (M2 to M5) and a common camera lens L. More specifically, a small animal (typically, a mouse) is placed as the sample A in the center of the fluorescence measurement device and observed from five angles so that five images of the sample A are formed on the common two-dimensional detector 38 by the common imaging lens L provided above the sample A. Light beams emitted from the sample A in the directions of observation angles other than 0°, that is, 72°, 144°, 216°, and 288° are reflected by the reflectors M2, M3, M4, and M5, respectively, and are then introduced into the imaging lens L so that images are formed on the common two-dimensional detector 38.

Figure 6:
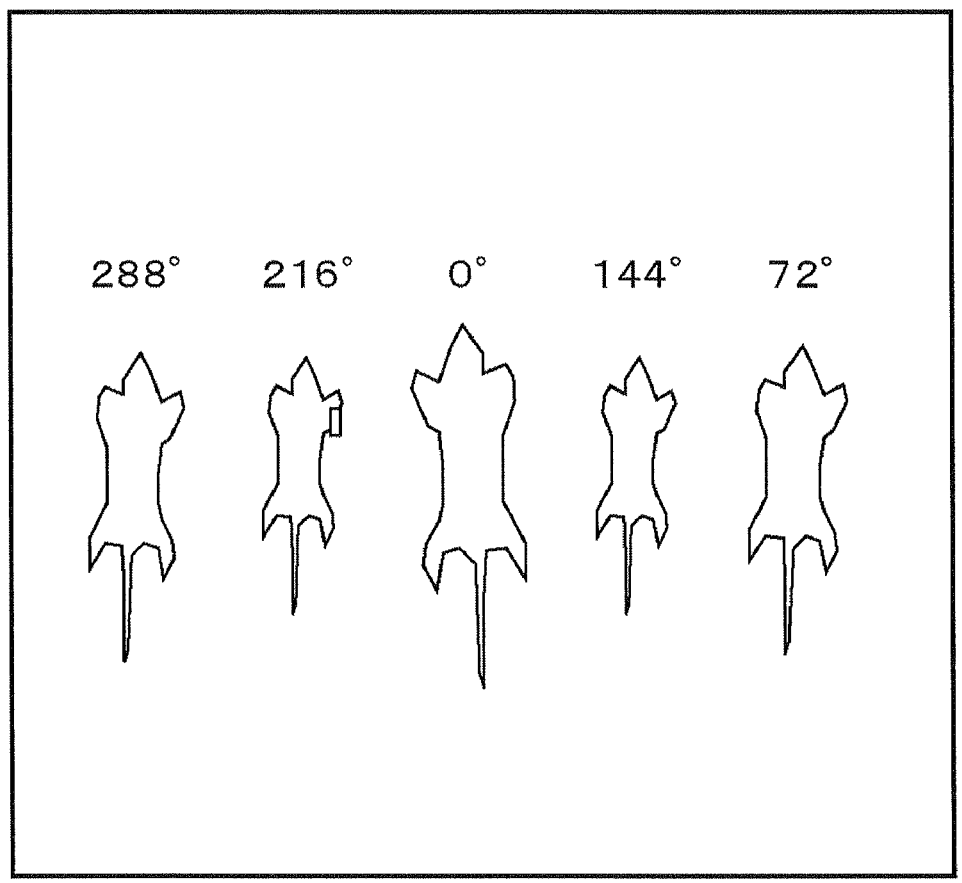
FIG. 6 is a plan view showing images formed on a two-dimensional detector of the fluorescence measurement device for a living body shown in FIG. 5.

The images formed on the CCD detector 38 are shown in FIG. 6. As shown in FIG. 6, these five images correspond to, from right to left, images observed from the 72°-direction, 144°-direction, 0°-direction (center), 216°-direction, and 288°-direction, respectively. The image observed from the 0°-direction arranged at the center is the largest because the light beam emitted in the 0°-direction is not reflected by a reflector, and therefore, the distance to the image formation lens is the shortest. On the other hand, the other four images are smaller in size than the image observed from the 0°-direction because the light beams emitted in the 72°-direction, 144°-direction, 216°-direction, and 288°-direction are reflected by the reflectors M2 to M5, and therefore, the distances from the virtual images of the sample are longer than the distance from the sample. In addition, these four images (72°, 144°, 216°, and 288°) are horizontally inverted. For these reasons, such images as shown in FIG. 6 are formed on the CCD detector 38. In this case, there is a problem that the light paths of the five light beams have different distances (light path lengths) due to the use of the reflectors M2 to M5, and therefore, unfocused images are formed on the CCD detector 38. However, such a problem can be solved by inserting auxiliary image formation lenses L1, L2, L3, L4, and L5 into the light paths of the five light beams, respectively. The auxiliary image formation lenses L1 to L5 have different focal lengths corresponding to the light path lengths of the light paths of the five light beams. In the case of this embodiment, the auxiliary image formation lenses L3 and L4 inserted into the light paths of the light beams emitted in the 144°-direction and the 216°-direction having the longest light path length are plane-parallel flat plates having no curvature. On the other hand, the auxiliary image formation lens L1 inserted into the light path of the light beam emitted in the 0°-direction having the shortest light path length is a slightly strong convex lens, and the auxiliary image formation lenses L2 and L5 inserted into the light paths of the light beams emitted in the 72°-direction and the 288°-direction having a light path length intermediate between the longest and shortest light path lengths are convex lenses of which curvature is smaller (i.e., whose focal length is longer) than that of the auxiliary image formation lens L1. That is, the auxiliary image formation lenses L1, L2, L3, L4, and L5 constitute, as a whole, a mosaic lens whose focal length is different from portion to portion. As described above, this embodiment achieves a simple structure having no moving parts and the formation of images of a sample observed from different angles on the common CCD detector 38 at one time.

Figure 7:
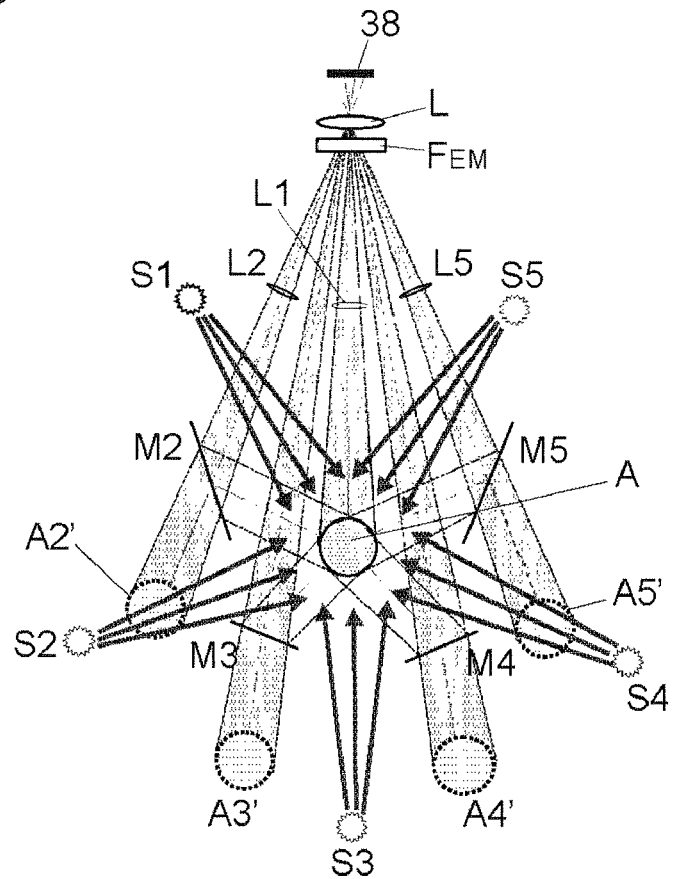
FIG. 7 is an elevation view of the fluorescence measurement device for a living body shown in FIG. 5 seen along the axial direction of a sample.

This observation technique will be described in more detail with reference to FIG. 7. In FIG. 7, a sample A is shown as a cylindrical article for the sake of brevity. The sample A is placed in the center of the fluorescence measurement device. Light beams emitted from the sample A in the directions of observation angles other than 0°, that is, 72°, 144°, 216°, and 288° are reflected by the reflectors M2, M3, M4, and M5, respectively so that virtual images A2', A3', A4', and A5' of the sample A are formed by the reflectors. Images of these virtual images are formed on the common two-dimensional detector (CCD detector) 38 by the imaging lens L provided above the sample A. Below the camera lens L, five images (A is a real image and the other four images A2', A3', A4', and A5' are virtual images) can be seen in five directions. As can be seen from FIG. 7, the distances to the virtual images A3' and A4' are the longest, the distances to the virtual images A2' and A5' are intermediate, and the distance to the real image A located in front of the camera lens L is the shortest. Accordingly in this case, when the camera lens L is focused on the virtual images A3' and A4', the images of the virtual images A2' and A5' and the real image A1 are defocused if nothing is done. Therefore, the images of the virtual images A2' and A5' are corrected by the auxiliary lenses (convex lenses) L2 and L5, respectively, and the image of the real image A is corrected by the auxiliary lens (convex lens) L1. On the CCD detector 38, the images shown in FIG. 6 are formed, that is, the images of the sample A observed at 72°, 144°, 0° (center), 216°, and 288° are formed in this order from right to left. These images formed on the CCD detector 38 are different in magnification because the distances between the camera lens L and the real image A and the virtual images A2', A3', A4', and A5' are different depending on observation angle. In addition, the images of the virtual images A2', A3', A4', and A5' are horizontally inversed. For these reasons, images as shown in FIG. 6 are formed.

A typical focal length of the image formation lens L is about 15 to 20 mm (for example, when the distance from the image formation lens L to the virtual image A3' of the sample is 300 mm and the magnification of the image of the sample formed on the CCD detector 38 is $1/15$, the distance between the center of the image formation lens L and the CCD detector 38 becomes 20 mm, which is calculated by multiplying 300 mm by a magnification of $1/15$, and therefore, the focal length of the image formation lens L is a little less than 20 mm). On the other hand, a typical focal length of each of the auxiliary image formation lenses L1, L2, and L5 determined by calculation is about 500 mm to 1500 mm. The reason for this is as follows. Let us define the distance between the sample A and the lens L as "a", and the distance between the virtual image A3' and the lens L as "b". The focal length of the auxiliary image formation lens L1 (defined as "f") is determined so that the light from the distance "a" (for example, "a"=200 mm), proceeds as if it comes from the distance "b" (for example, "b"=300 mm), i.e., the distance 200 mm is transformed to the distance 300 mm by the lens L1. So the focal length "f" can be determined by the following simple image formation formula: $(1/f) = (1/a) - (1/b)$. In this case, the focal length "f" determined by this image formation formula is 600 mm. On the other hand, the focal length of the auxiliary image formation lens L2 (L5) is set so that a distance between the virtual image A2' (A5') and the lens L of about 250 mm is transformed to 300 mm which is the distance between the virtual image A3' and the lens L. Therefore, after the similar calculation, the focal length of the lens L2 (L5) becomes 1500 mm, which is much longer than that of the lens L1. As described above, lenses having focal lengths longer than that of the lens L, that is, lenses having extremely small curvatures suffice as the auxiliary image formation lenses L1, L2, and L5.

<Examples of Combination of Multidirectional Observation-Type Fluorescence Measurement Device and Multidirectional Irradiating Units>

Figure 5:
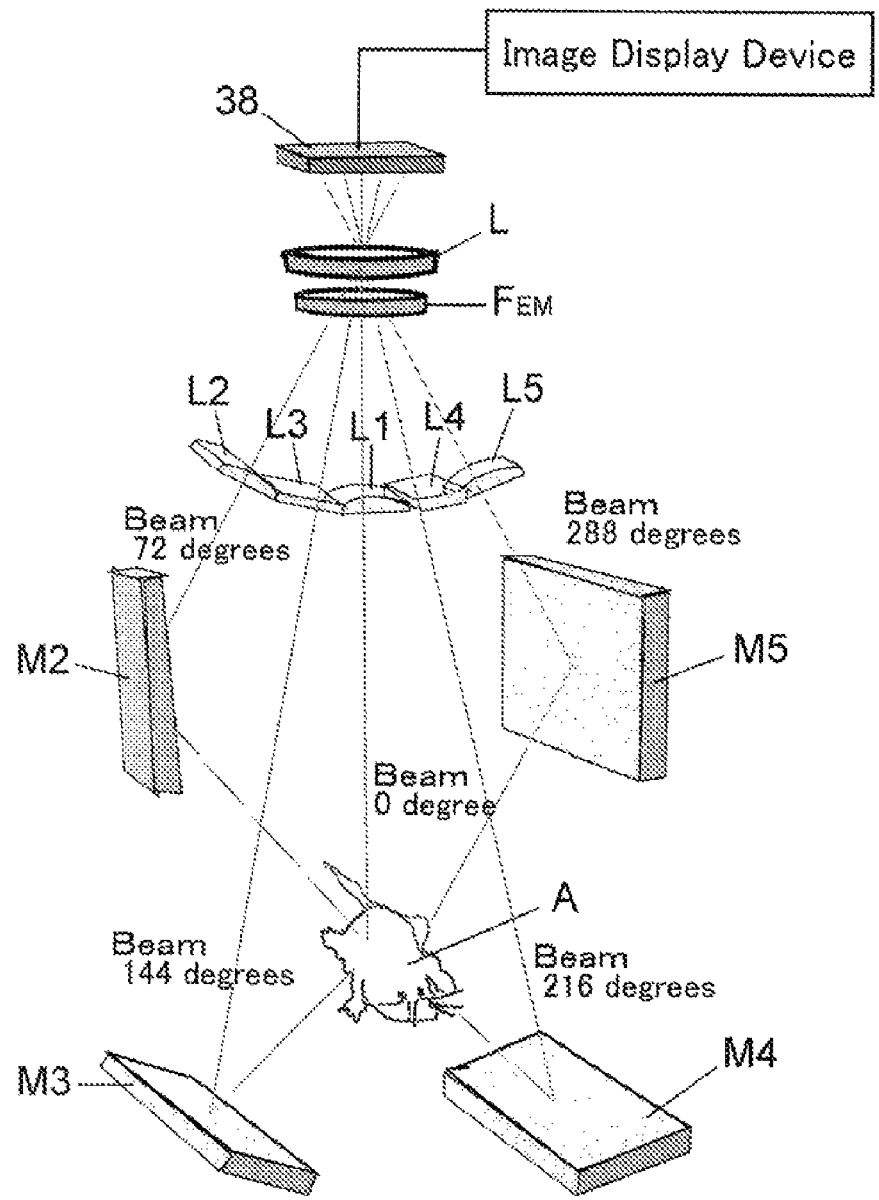
FIG. 5 is a schematic perspective view of a main part of another embodiment of a fluorescence measurement device for a living body.

Referring to FIG. 7 again, irradiating units S1, S2, S3, S4, and S5 not shown in FIG. 5 are shown in the elevation view. As these irradiating units, those having the structure described above with reference to FIG. 2, 3, or 4 can be used. These five irradiating units S1, S2, S3, S4, and S5 are placed around the sample A so that the sample A is irradiated with light from five different angles. In this case, there is an advantage that there exist, among the reflectors M2, M3, M4 and M5, proper spaces to be assigned to the irradiating units S1, S2, S3, S4, and S5 in the fluorescence measurement device. In the case of observation from five directions evenly spaced around the sample A and the virtual images A2', A3', A4', and A5' of the sample A are formed every 72°, and therefore, excitation light with which the sample A is irradiated forms an angle of +36° or −36° with a principal ray emitted from the sample A and traveling directly toward the center of the front lens L or toward the center of the reflector M2, M3, M4, or M5. In the case of observation from six or seven directions evenly spaced around the sample, the angle which the direction of excitation light forms with the principal ray is ±30° or ±25.714°, respectively, which is an irradiation angle suitable for measuring fluorescence.

In the case of fluorescence measurement, the wavelength of light emitted from each of the irradiating units S1, S2, S3, S4, and S5 is usually selected according to the absorption wavelength of a fluorescence probe having specificity to a molecular species or a tumor of interest. In this example, wavelength selection can be easily performed by ON/OFF switching of an electrical circuit of a laser diode (LD) included in the irradiating unit. A fluorescence filter $F_{EM}$ is provided just before the camera lens L to detect only the wavelength component within the spectral pass band of the filter $F_{EM}$, separating from all the fluorescence light that comes from the sample A by irradiation with excitation light. If some parts of the wavelength components of excitation light leak through the filter after being scattered with their wavelengths unchanged and then are detected, such wavelength components become background light and interfere with observation. Therefore, the selection of the wavelength of excitation light emitted from the light sources and the selection of the transmission characteristics of the fluorescence filter $F_{EM}$ are important to completely prevent the passage of wavelength components of the excitation light through the fluorescence filter $F_{EM}$.

After the completion of selection of the wavelength of light emitted from the irradiating unit, a desired irradiation direction can be easily selected from five irradiation directions by turning on a desired one of the irradiating units S1, S2, S3, S4, and S5. In this case, there are some choices for turning on/off exciting light to observe the sample A from five directions while fluorescence excitation is performed. A first choice is the simplest measurement method. More specifically, the laser diodes of all the irradiating units S1, S2, S3, S4, and S5 arranged in five irradiation directions are turned on at the same time, that is, the sample A is always irradiated with exciting light from five directions covering 360° to pick up (record) five images formed on the CCD detector 38 as shown in FIG. 6.

A second choice is a method in which the irradiating units S1, S2, S3, S4, and S5 are turned on one by one, that is, exposure is performed five times. In this case, it is possible to obtain not only the fluorescence images of the sample A irradiated with exciting light from the front side of the sample A but also the fluorescence images of the sample A irradiated with exciting light from only the back or lateral side of the sample A. That is, it is possible to obtain 25 images of the sample A in total by performing exposure 5 times because 5 images of different observing directions obtained by one exposure are repeated five times by changing irradiation angle.

Figure 8A:
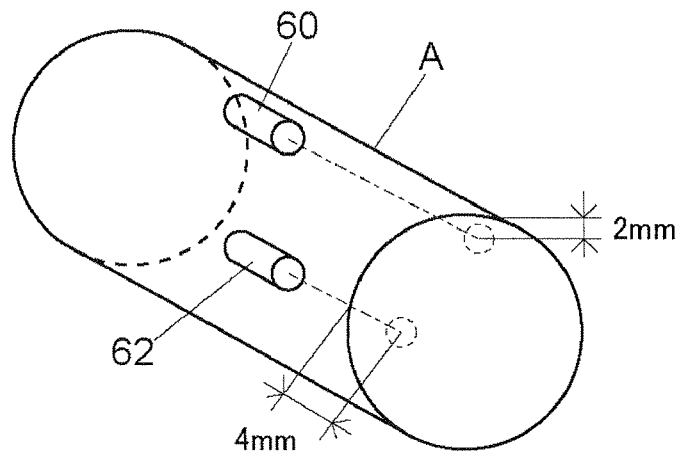
FIG. 8A is a perspective view of a simulated sample to be measured.
Figure 8B:
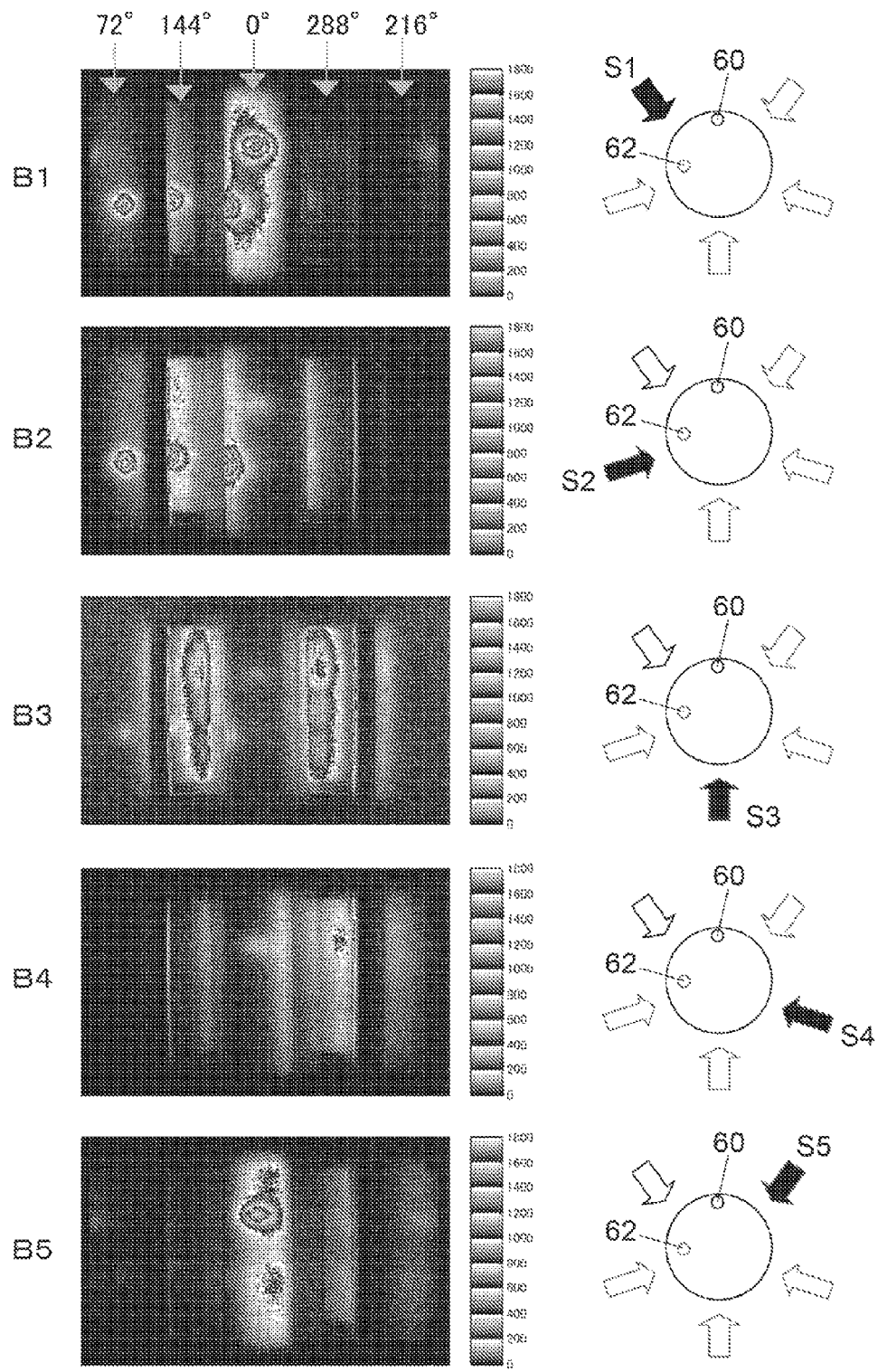

A measurement example demonstrating the effectiveness of switching among five different irradiation directions will be described with reference to FIGS. 8A and 8B. As shown in FIG. 8A, a cylindrical phantom with a diameter of 25 mm and a length of 150 mm simulating a mouse is used as a sample A, which has an absorption/scattering coefficient similar to that of a living body. Further, two micro-fluorescence sources 60 and 62 are embedded in the phantom at positions shown in FIG. 8A having depths of 2 mm and 4 mm. The images of the phantom were taken by the simultaneous five-direction observation device shown in FIG. 7 which can switch among five irradiation directions. More specifically, images of the sample A observed from five directions were obtained by turning on the irradiating units S1 to S5 arranged in five different directions in order to switch an irradiation direction. As shown in FIGS. 8B1 to 8B5, 25 images were obtained in total. It is to be noted that in FIG. 8B, fluorescence intensity is indicated by a gray-scale bar displayed on the right-hand side. The gray-scale bar has repeated gray scale representation such as 0-200, 200-400 and so on. More specifically, the weakest range from black to white corresponds to a gray scale range from 0 to 200, the next range from black to white corresponds to a gray scale from 200 to 400, and the next range from black to white corresponds to a gray scale from 400 to 600. In this way, fluorescence intensity is indicated by the repeated gray scale, and therefore, a location having a larger number of black and white fringes indicates higher fluorescence intensity. As can be clearly seen, measured fluorescence intensities of the two micro-fluorescence sources 60 and 62 vary depending on the relationship between the position of the fluorescence source and the irradiation direction of exciting light. For example, as shown in FIG. 8B1, when the sample A is irradiated with exciting light emitted from the irradiating unit S1, in the image observed from the 0° direction, very strong fluorescence emitted from the fluorescence source 60 embedded at a small depth of 2 mm is detected and quite strong fluorescence emitted from the fluorescence source 62 embedded at a depth of 4 mm is also detected, and in the image observed from the 72° direction, relatively strong fluorescence emitted from the fluorescence source 62 embedded at a depth of 4 mm is detected. When the irradiating unit 51 is changed to the irradiating unit S2, as shown in FIG. 8B2, in the image observed from the 72° direction and the image observed from the 144° direction, strong fluorescence emitted from the fluorescence source 62 embedded at a depth of 4 mm is detected, and in the image observed from the 0° direction, strong fluorescence emitted from the fluorescence source 62 embedded at a depth of 4 mm is detected and weak fluorescence emitted from the fluorescence source 60 embedded at a depth of 2 mm is detected. When the irradiating unit S2 is changed to the irradiating unit S3, as shown in FIG. 8B3, fluorescence is weak on the whole because the sample A is irradiated from the back side of the sample A. However, looking carefully at the image observed from the 0° direction, weak fluorescence emitted from the fluorescence source 60 embedded at a depth of 2 mm can be detected. It is to be noted that relatively strong fluorescence detected in the image observed from the 144° direction and the image observed from the 288° direction is one emitted from the phantom body itself. When the irradiating unit S3 is changed to the irradiating unit S4, as shown in FIG. 8B4, fluorescence emitted from the fluorescence source 60 embedded at a small depth of 2 mm is detected only in the image observed from the 0° direction. Further, when the irradiating unit S4 is changed to the irradiating unit S5, as shown in FIG. 8B5, very strong fluorescence emitted from the front fluorescence source 60 embedded at a depth of 2 mm is detected only in the image observed from the 0° direction.

The result shown in FIG. 8B indicates that the intensity of fluorescence and how fluorescence appears are regularly changed depending on whether a fluorescence source in the body of a sample animal is present at a shallow or great depth. That is, the depth of the fluorescence source can be estimated from the intensity of fluorescence detected in images. Generally, when a fluorescence source is present at a relatively shallow depth, a bright small spot of fluorescence is detected in a subject in any one of 25 images. On the other hand, when a fluorescence source is present at a great depth, weak diffused fluorescence is detected in all the 25 images. Further, a method for imaging the distribution of fluorescence sources to some extent can also be provided by using an appropriate algorithm for inverse problems. As can be seen from the result shown in FIG. 8B, the difference in the irradiation direction of exciting light defines how fluorescence appears, which indicates the effectiveness of the fluorescence measurement device capable of easily selecting the irradiation direction of exciting light.

It is to be noted that, in addition to the above irradiation pattern, various other irradiation patterns may be possible. For example, the sample A may be irradiated from two directions at the same time. In any case, the important point of the present invention is that a direction in which exciting light is emitted can be freely switched without using movable parts simply by ON/OFF switching of the irradiating units so that the sample is irradiated with exciting light from the front, lateral, back, diagonally front, and/or diagonally back side(s) thereof. As described above, when each of the irradiating units has two or more light sources with different wavelengths as shown in FIG. 3, selection of an excitation wavelength can be performed simply by electrical ON/OFF switching of the light sources. In this case, an exciting-light irradiating system needs no movable parts.

What is claimed is:

1. A fluorescence measurement device for a living body, comprising:
   an exciting light-irradiating device having a plurality of exciting light sources placed at mutually different positions for irradiating the sample with exciting light from various different directions;
   an electrical switch for controlling lighting of the exciting light sources;
   a fluorescence filter allowing only predetermined wavelength components of fluorescence emitted from a living sample placed on a sample holder to pass through;
   a two-dimensional detector for picking up a fluorescence image produced by fluorescence passed through the fluorescence filter;
   an image display device for displaying an image picked up by the detector, and
   a light guide optical system for guiding a plurality of fluorescence images to the two-dimensional detector to observe fluorescence emitted from the sample placed on the sample holder from a plurality of directions;
   wherein each of the exciting light sources of the exciting light-irradiating device has an optical filter for eliminating, from exciting light emitted from the exciting light source, at least wavelength components that are the same as that allowed to pass through the fluorescence filter.

2. The fluorescence measurement device for a living body according to claim 1, wherein a wavelength of exciting light is switchable by ON/OFF switching of the plurality of exciting light sources by the electrical switch.

3. The fluorescence measurement device for a living body according to claim 1, wherein an irradiation direction of exciting light emitted toward the sample is selectable by ON/OFF switching of the plurality of exciting light sources by the electrical switch.

* * * * *